United States Patent [19]

Pontagnier et al.

[11] Patent Number: 4,668,681
[45] Date of Patent: May 26, 1987

[54] 2-(4-PHENYLPIPERAZINYLETHYL) ANILINES

[75] Inventors: Henri Pontagnier, Pessac; Marie-Hélène Creuzet, Bordeaux; Claude Feniou, Pessac; Françoise Guichard, Bordeaux; Gisèle Prat, Talence, all of France

[73] Assignee: Societe Cortial, S.A., Paris, France

[21] Appl. No.: 843,915

[22] Filed: Mar. 21, 1986

Related U.S. Application Data

[62] Division of Ser. No. 439,041, Nov. 3, 1982, abandoned.

[30] Foreign Application Priority Data

Nov. 3, 1981 [FR] France ............... 81 20564

[51] Int. Cl.⁴ .......................... A61K 31/495
[52] U.S. Cl. ........................... 514/255; 514/253; 544/377; 544/398; 544/402
[58] Field of Search ................ 514/255, 253

[56] References Cited

U.S. PATENT DOCUMENTS

| | | | |
|---|---|---|---|
| 3,562,277 | 2/1971 | Hansen et al. | 544/377 |
| 3,928,358 | 12/1975 | Renth et al. | 544/377 |
| 3,981,864 | 9/1976 | Tanaka et al. | 544/377 |
| 4,094,980 | 1/1978 | Renth et al. | 544/377 |

FOREIGN PATENT DOCUMENTS

| | | | |
|---|---|---|---|
| 1314913 | 12/1962 | France | 544/394 |
| 191 | 2/1968 | France . | |
| 208 | 7/1968 | France . | |
| 2476644 | 8/1981 | France . | |
| 0078756 | 5/1983 | France | 544/377 |
| 0078757 | 5/1983 | France | 544/377 |
| 953005 | 3/1964 | United Kingdom | 544/394 |

Primary Examiner—Glennon H. Hollrah
Assistant Examiner—James H. Turnipseed
Attorney, Agent, or Firm—Oblon, Fisher, Spivak, McClelland & Maier

[57] ABSTRACT

This invention relates to 2-(4-phenylpiperazinylethyl)anilines, to methods for preparing them and to their uses in medical therapy.

These compounds have the following general formula

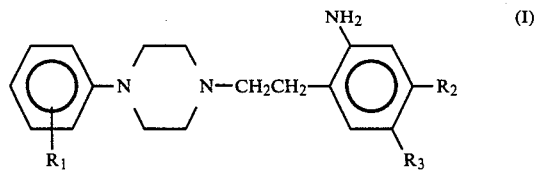

wherein $R_1$ represents one or more substituents selected from the group consisting of H, $CH_3$, $CF_3$, F, Cl, and $OCH_3$; $R_2$ and $R_3$, which may be the same or different, and are selected from the group consisting of H and ($C_1$–$C_4$) alkoxy, or $R_2$ and $R_3$ taken together can form a chain selected from the group consisting of —O—($CH_2$)$_n$—O—, wherein n=1 or 2 and —O—$CH_2$—O—$CH_2$ with the proviso that $R_1$ is not meta $CF_3$ when $R_2=R_3=H$, and pharmaceutically non-toxic salts thereof. The compounds of this invention are useful in the treatment of allergic and anaphylatic conditions and motion sickness.

7 Claims, No Drawings

2-(4-PHENYLPIPERAZINYLETHYL) ANILINES

BACKGROUND OF THE INVENTION

1. Field of the Invention

This invention relates to 2-(4-phenylpiperazinylethyl)anilines, to the preparation thereof and to their use in medical therapy.

2. Description of the Prior Art

Certain derivatives of 3- and 4-(4-phenylpiperazinylethyl)aniline are known, such as those disclosed in French Special Medicament Patents Numbers 191M and 208M. Derivatives of 2-piperazinylaniline substituted at the 4-nitrogen of the piperazine ring with a methyl group are also known (French Patent Application Number 80 03774, now French Pat. No. 2,476,644). The compounds previously disclosed in French Patent Application No. 80 03774 exhibit psychotropic activity of the anxiolytic and antidepressor type. However, it has not been known that compounds of this type have antihistaminic and antiallergic activities which might permit their use in medical therapy and in particular in allergology.

The known synthetic antihistamines belong principally to the following chemical families: phenothiazine (promethazine), cycloheptane (cyproheptadine), ethylenediamine (antazoline), aminoethanol (doxylamine), propylamine (tripolidine), and diphenyl methylpiperazine (cinnarizine). However, no antihistamines are known having a structural formula resembling the compounds of this invention.

SUMMARY OF THE INVENTION

Accordingly, it is an object of this invention to provide new antihistamine compounds. Other objects of the invention will become apparent from the description which follows.

The compounds of the invention have the formula

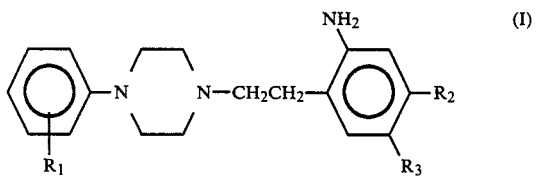

(I)

wherein $R_1$ represents one or more substituents in the ortho, meta, or para positions selected from the group consisting of H, $CH_3$, $CF_3$, F, Cl and $OCH_3$; $R_2$ and $R_3$ may be the same or different, and are selected from the group consisting of H, ($C_1$–$C_4$) alkoxy, or $R_2$ and $R_3$ taken together can form a chain selected from the group consisting of —O—$(CH_2)_n$—O—, wherein n=1 or 2, and —O—$CH_2$—O—$CH_2$—.

These compounds can be used in the form of the free base or in the form of their pharmacologically acceptable salts such as the hydrochlorides, citrates and benzylates.

DETAILED DESCRIPTION OF THE PREFERRED EMBODIMENTS

The compounds of formula (I) are generally prepared by a reaction between a 2-(2-haloethyl)-1-nitrobenzene and an N-phenylpiperazine, followed by a reduction of the nitro derivative so obtained.

The substituted $R_1$ may be located ortho, meta, or para to the bond with the piperazine ring.

Having generally described the invention, a more complete understanding can be obtained by reference to certain specific examples which are provided herein for purposes of illustration only and are not intended to limiting unless otherwise specified.

EXAMPLES

Example 1

Preparation of 2-(4-phenylpiperazinylethyl)aniline

A mixture comprising 0.1 moles of 2-(2-bromoethyl)-1-nitrobenzene, 0.23 moles of N-phenylpiperazine and 300 cm³ of absolute ethanol is heated at the reflux temperature of the ethanol with agitation for 15 hours. The alcohol is then removed by evaporation. The residue from the evaporation is taken up in water and an ether extraction is conducted. The ether phase is washed with water, dried over $Na_2SO_4$, and the ether is removed by evaporation. The excess phenylpiperazine is removed by distillation. The residue from the distillation is recrystallized from methanol. 1-Nitro-2-(4-phenylpiperazinyl)-ethylbenzene is thus obtained having a melting point of 76° C.

This nitro derivative is dissolved in methanol, and 7–8 g of Raney nickel are added to the solution. The mixture is agitated under a hydrogen atmosphere until the reaction is complete. The Raney nickel is removed by filtration; the solvent is removed by evaporation.

2-(4-phenylpiperazinylethyl)aniline is obtained by crystallization of the evaporation residue from a mixture of ethyl ether and petroleum ether. MP 103° C.

Example 2

By the procedure of Example 1 a number of derivatives of the formula

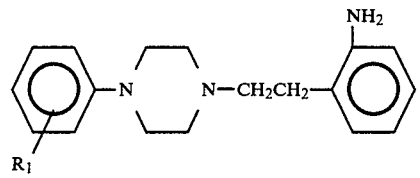

are prepared. The $R_1$ substituents and their corresponding melting points are given in Table 1.

TABLE 1

| | | |
|---|---|---|
| $R_1$ = 4-F | M.P. | 113° C. |
| $R_1$ = 3-$CF_3$ | M.P. | 64° C. |
| $R_1$ = 2-$OCH_3$ | M.P. | 103° C. |
| $R_1$ = 4-Cl | M.P. | 126° C. |
| $R_1$ = 2-$CH_3$ | M.P. | 97° C. |

Example 3

Preparation of 4,5-methylenedioxy-2-(4-(3-trifluoromethylphenyl)-piperazinylethyl)aniline A mixture comprised of 22.9 g of 6-(2-chloroethyl)-5-nitrobenzodioxole-1,3, 69 g of N-(3-trifluoromethylphenyl)piperazine and 150 cm³ of ethanol is heated at 120° C. with agitation for 18 hours. The ethanol is removed by evaporation, and the residue is taken up in ethyl ether and water. The ether phase is separated by decantation, then extracted with a 2N aqueous solution of hydrochloric acid. The hydrochloride of the 5-nitro- 6-(4-(3-trifluoromethylphenyl)piperazinylethyl)benzodioxole-1,3 partially precipitates. The precipitate is filtered and the filtered precipitate and the acid aqueous phase are recombined and made alkaline. After the solution is made alkaline it is extracted with ethyl ether, followed by drying over $Na_2SO_4$. The ether is removed by evaporation and the residue is recrystallized from ethyl ether. MP 91° C.

A quantity of 27 g of the nitro derivative so prepared is suspended in 1.5 l of methanol, and 7–8 g of Raney nickel are added. The mixture is agitated under a hydrogen atmosphere until the reaction is complete. The Raney nickel is removed by filtration. The filtrate is evaporated and the residue of the evaporation is recrystallized from a mixture of ethyl ether and petroleum ether. The product obtained is 4,5-methylenedioxy-2-(4-(3-trifluoromethylphenyl)-piperazinylethyl)aniline, which is purified by recrystallization from methanol. MP 88° C.

In Table 2 below the principal features of the NMR spectra of the compounds prepared according to Examples 1, 2 and 3 in solution in $CDCl_3$ are given. The chemical shifts are given relative to TMS internal standard, together with the number of protons and the multiplicity of the peaks wherein:
cm = complex multiplet,
s = singlet,
b = broad peak.

The compounds of the invention were subjected to various pharmacological tests and the results are given below.

The lethality produced by the compounds of this invention was measured in the Swiss mouse free from specific pathogenic organisms. After a period of observation of 14 days, the $LD_{50}$, by oral administration, of the compound of Example 1 administered as a 20% solution in Tween (a polysorbate detergent) is 1175 (946–1459) mg/kg.

The antihistaminic activity was measured in vitro by measuring the concentration which produced 50% inhibition of the contractions induced by histamine ($1 \times 10^{-8}$ g/l) in the isolated ileum of the guinea pig ($IC_{50}$). The $IC_{50}$ for the compound of Example 1, by the bathing method, is 6.3 (4.14–9.58)$\times 10^{-6}$ g/ml.

The antiallergic activity was determined by the passive cutaneous anaphylaxis test in the following manner. A quantity of 0.1 ml of serum containing IgE was administered intradermally to male Sprague-Dawley rats. The serum was prepared by sensitizing Sprague-Dawley rats by an intraperitoneal injection of ovalbumin and a suspension of *Bordetella pertussis* followed after 20 days by a second injection of ovalbumin. 24 Hours after administration of the serum, 0.5 ml of a solution containing 8.25 mg/kg of ovalbumin and 26.4 mg/kg of Evans blue in a pH 7.05 buffer was administered intravenously. After 30 minutes the animals were sacrificed. Each papule was dissected, weighed and incubated for four days at 37° C. in 15 g of formamide. The amount of Evans blue contained in each papule was determined by measuring the optical density of the mixture. The product to be tested was administered orally in a homogenous suspension in the presence of Tween 80, ten minutes before the releasing injection. Its activity is evaluated by the percentage decrease of the amount of Evans blue which has diffused in the papule. For the compound of Example 1 the $ED_{50}$ is 5.11 (3.39–7.76) mg/kg.

Considering their antihistaminic and antianaphylactic activities combined with a low toxicity, the compounds of the present invention are useful in medical therapy, alone or in combination, in the treatment of allergic and anaphylactic states such as urticaria, pruritus, dermatosis, eczema, hay fever, Quinke's edema, serum sickness, asthma, and anaphylactic shock. They can also be used as a preventative or therapeutic agent in treating motion sickness.

They can be administered orally in the form, for example, of dragees, tablets, syrups, ampules, rectally in the form of a suppository, intramuscularly or intravenously or topically in the form of a pomade of gel. The doses to be administered will vary according to the indication and the subject and will range from 2 to 200 mg/day in two to six doses orally, from 2 to 200 mg/day in one or two doses rectally, and from 0.5 to 50 mg per injection for parenteral administration.

Having now fully described the invention, it will be apparent to one of ordinary skill in the art that many changes and modifications can be made thereto without departing from the spirit or scope of the invention as set forth herein.

TABLE 2

| $R_1$ | $R_2, R_3$ | NH$_2$ —CH$_2$— | NH$_2$ | Aromatic protons | others |
|---|---|---|---|---|---|
| H | H,H | 2.5–3.3 ppm; 12H; cm | 3.9 ppm; 2H; b | 6.4–7.4 ppm; 9H; cm | |
| 2-CH$_3$ | H,H | 2.3–3.2 ppm; 12H; cm | 3.9 ppm; 2H; b | 6.4–7.3 ppm; 8H; cm | 2.2 ppm; 3H; s CH$_3$—C |
| *4-Cl | H,H | 2.5–3.4 ppm; 12H; cm | 4.2 ppm; 2H; b | 6.5–7.4 ppm; 8H; cm | |
| 2-OCH$_3$ | H,H | 2.5–3.3 ppm; 12H; cm | 4.0 ppm; 2H; b | 6.5–7.2 ppm; 8H; cm | 3.8 ppm; 3H; s CH$_3$—O |
| 4-F | H,H | 2.5–3.3 ppm; 12H; cm | 3.9 ppm; 2H; b | 6.5–7.2 ppm; 8H; cm | |
| 3-CF$_3$ | —O—CH$_2$—O— | 2.4–3.4 ppm; 12H; cm (CH$_2$CH$_2$—N) 5.8 ppm; 2H; s (—O—CH$_2$—O—) | 3.7 ppm; 2H; b | 6.2 and 6.5 ppm; 2H; s (H of the aniline ring) 6.9–7.5 ppm; 4H; cm (H of the phenyl-piperazine ring) | |

*Solvent CDCl$_3$ + 3 drops of DMSO-D6

What is claimed as new and desired to be secured by Letters Patent of the United States is:

1. A method of treating allergic conditions, comprising administering to a patient afflicted with an allergic condition an antiallergic effective amount of at least one compound of the formula

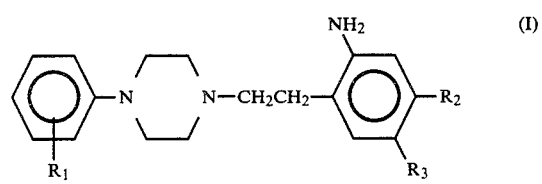

and pharmaceutically acceptable nontoxic acid addition salts thereof, wherein:

$R_1$ represents one or more substituents selected from the group consisting of H, CH$_3$, CF$_3$, F, Cl, and OCH$_3$;

$R_2$ and $R_3$ may be the same or different, and are selected from the group consisting of H and (C$_1$-C$_4$) alkoxy, or $R_2$ and $R_3$ taken together may form a chain selected from the group consisting of —O—(CH$_2$)$_n$—O—, wherein n=1 or 2, and —O—CH$_2$—O—CH$_2$—, with the proviso that $R_1$ is not meta-CF$_3$ when $R_2$=$R_3$=H.

2. A method of treating motion sickness, comprising administering to a patient susceptible to motion sickness an anti-motion sickness effective amount of at least one compound of the formula

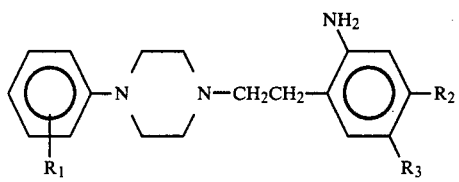

and pharmaceutically acceptable nontoxic acid addition salts thereof, wherein:

$R_1$ represents one or more substituents selected from the group consisting of H, CH$_3$, CF$_3$, F, Cl, and OCH$_3$;

$R_2$ and $R_3$ may be the same or different, and are selected from the group consisting of H and (C$_1$-C$_4$) alkoxy, or $R_2$ and $R_3$ taken together may form a chain selected from the group consisting of —O—(CH$_2$)$_n$—O—, wherein n=1 or 2, and —O—CH$_2$—O—CH$_2$—, with the proviso that $R_1$ is not meta-CF$_3$ when $R_2$=$R_3$=H.

3. A method of treating anaphylactic conditions, comprising administering to a patient susceptible to an anaphylactic condition an anti-anaphylactic effective amount of at least one compound of the formula

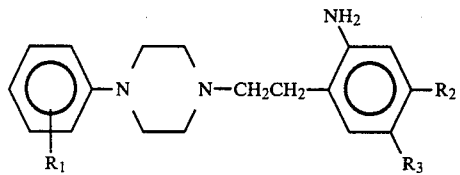

and pharmaceutically acceptable nontoxic acid addition salts thereof, wherein:

$R_1$ represents one or more substituents selected from the group consisting of H, CH$_3$, CF$_3$, F, Cl, and OCH$_3$;

$R_2$ and $R_3$ may be the same or different, and are selected from the group consisting of H and (C$_1$-C$_4$)alkoxy, or $R_2$ and $R_3$ taken together may form a chain selected from the group consisting of —O—(CH$_2$)$_n$—O—, wherein n=1 or 2, and —O—CH$_2$—O—CH$_2$—, with the proviso that $R_1$ is not meta-CF$_3$ when $R_2$=$R_3$=H.

4. A method of decreasing histaminic activity, comprising administering to a patient susceptible to increased histaminic activity an anti-histamine effective amount of at least one compound of the formula

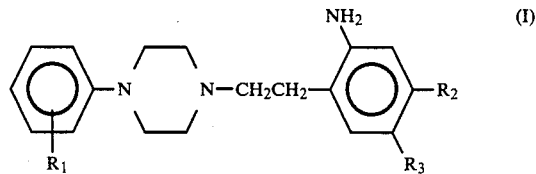

and pharmaceutically acceptable nontoxic acid addition salts thereof, wherein:

$R_1$ represents one or more substituents selected from the group consisting of H, CH$_3$, CF$_3$, F, Cl, and OCH$_3$;

$R_2$ and $R_3$ may be the same or different, and are selected from the group consisting of H and (C$_1$-C$_4$)alkoxy, or $R_2$ and $R_3$ taken together may form a chain selected from the group consisting of —O—(CH$_2$)$_n$—O—, wherein n=1 or 2, and —O—CH$_2$—O—CH$_2$—, with the proviso that $R_1$ is not meta-CF$_3$ when $R_2$=$R_3$=H.

5. The method of claim 1 wherein the allergic conditions are associated with a condition selected from the group consisting of urticaria, pruritus, dermatosis, eczema, hay fever, Quinke's edema, serum sickness, asthma and anaphylactic shock.

6. The method of claim 3, wherein the anaphylactic condition is associated with a condition selected from the group consisting of urticaria, pruritus, dermatosis, eczema, hay fever, Quinke's edema, serum sickness, asthma and anaphylactic shock.

7. The method of claim 4, wherein the histaminic activity is associated with a condition selected from the group consisting of urticaria, pruritus, dermatosis, eczema, hay fever, Quinke's edema, serum sickness, asthma and anaphylactic shock.

* * * * *